(12) United States Patent
Zachariasen (10) Patent No.: US 11,364,138 B2
(45) Date of Patent: *Jun. 21, 2022

(54) USE OF ADDITIVE MANUFACTURING PROCESSES IN THE MANUFACTURE OF CUSTOM ORTHOSES

(71) Applicant: 3D Patents, LLC, Talent, OR (US)

(72) Inventor: Joseph T. Zachariasen, Medford, OR (US)

(73) Assignee: 3D Patents, LLC, Medford, OR (US)

(*) Notice: Subject to any disclaimer, the term of this patent is extended or adjusted under 35 U.S.C. 154(b) by 390 days.

This patent is subject to a terminal disclaimer.

(21) Appl. No.: 16/681,785

(22) Filed: Nov. 12, 2019

(65) Prior Publication Data
US 2020/0078202 A1    Mar. 12, 2020

Related U.S. Application Data

(63) Continuation of application No. 15/479,107, filed on Apr. 4, 2017, now Pat. No. 10,470,912, which is a
(Continued)

(51) Int. Cl.
*A61F 5/01* (2006.01)
*G06F 17/50* (2006.01)
(Continued)

(52) U.S. Cl.
CPC .............. *A61F 5/0111* (2013.01); *A61F 5/01* (2013.01); *B29C 64/386* (2017.08); *B33Y 10/00* (2014.12);
(Continued)

(58) Field of Classification Search
CPC .......... A61F 5/0111; A61F 5/01; B29C 64/00; B29C 64/386; B33Y 80/00; B33Y 10/00;
(Continued)

(56) References Cited

U.S. PATENT DOCUMENTS

| 5,432,703 A | 7/1995 | Clynch et al. |
| 6,141,889 A | 11/2000 | Baum |

(Continued)

FOREIGN PATENT DOCUMENTS

| GB | 2508204 A | 5/2014 |
| WO | 2014080217 A1 | 5/2014 |

OTHER PUBLICATIONS

USPTO, International Search Report and Written Opinion, International application No. PCT/US2013/077589, dated Mar. 19, 2014.
(Continued)

*Primary Examiner* — Tarla R Patel (74) *Attorney, Agent, or Firm* — Dentons, Durham, Jones, Pinegar (57) ABSTRACT

A method for manufacturing a custom wearable medical device, such as an orthosis (e.g., an ankle brace, etc.), includes use of scanning processes. A digital model of a surface may be generated from data corresponding to a body part for which the customer wearable medical device is to be fabricated, and then applied to a digital device model to define a custom digital device model. The digital device model and, thus, the custom digital device model may include one or more standard features. The custom digital device model may be used with an automated manufacturing process to make some or all of the custom wearable medical device. In some embodiments, additive manufacturing processes may be used to form a portion or all of the custom wearable medical device.

20 Claims, 4 Drawing Sheets

Related U.S. Application Data continuation of application No. 14/139,489, filed on Dec. 23, 2013, now Pat. No. 9,610,731.

(60) Provisional application No. 61/800,582, filed on Mar. 15, 2013, provisional application No. 61/745,557, filed on Dec. 22, 2012.

(51) Int. Cl.
    | | | |
    |---|---|---|
    | *B33Y 10/00* | (2015.01) | |
    | *B33Y 50/02* | (2015.01) | |
    | *B33Y 80/00* | (2015.01) | |
    | *G05B 19/4097* | (2006.01) | |
    | *B29C 64/00* | (2017.01) | |
    | *B29C 64/386* | (2017.01) | |
    | *B29L 31/00* | (2006.01) | |
    | *B29L 31/08* | (2006.01) | |
    | *G06F 30/00* | (2020.01) | |

(52) U.S. Cl.
    CPC ............ *B33Y 50/02* (2014.12); *B33Y 80/00* (2014.12); *G05B 19/4097* (2013.01); *G06F 30/00* (2020.01); *B29L 2031/085* (2013.01); *B29L 2031/753* (2013.01); *B29L 2031/7532* (2013.01); *G05B 2219/35134* (2013.01); *G05B 2219/49007* (2013.01); *Y02P 70/50* (2015.11)

(58) Field of Classification Search
    CPC ............ B33Y 50/02; G05B 19/4097; G05B 2219/35134; G05B 2219/49007; G06F 17/50; B29L 2031/753; B29L 2031/7532; B29L 2031/085; Y02P 70/523
    See application file for complete search history.

(56) References Cited

U.S. PATENT DOCUMENTS

| | | | |
|---|---|---|---|
| 6,155,997 | A | 12/2000 | Castro |
| 6,402,713 | B1 | 6/2002 | Doyle |
| 6,463,351 | B1 | 10/2002 | Clynch |
| 8,409,122 | B2 | 4/2013 | Cropper et al. |
| 8,538,570 | B2 | 9/2013 | Stanhope et al. |
| 8,838,263 | B2 | 9/2014 | Sivak et al. |
| 9,469,075 | B2 * | 10/2016 | Zachariasen ............ B33Y 30/00 |
| 9,610,731 | B2 * | 4/2017 | Zachariasen ............ G06F 30/00 |
| 10,470,912 | B2 * | 11/2019 | Zachariasen ............ B33Y 50/02 |
| 10,675,855 | B2 * | 6/2020 | Zachariasen ............ G06F 30/17 |
| 2002/0010408 | A1 | 1/2002 | Pomatto et al. |
| 2007/0016323 | A1 | 1/2007 | Fried |
| 2007/0118243 | A1 | 5/2007 | Schroeder et al. |
| 2007/0133850 | A1 | 6/2007 | Paez |
| 2008/0292179 | A1 | 11/2008 | Busch |
| 2009/0306801 | A1 | 12/2009 | Sivak et al. |
| 2010/0094174 | A1 | 4/2010 | Choi et al. |
| 2010/0113980 | A1 | 5/2010 | Herr et al. |
| 2010/0262054 | A1 | 10/2010 | Summit et al. |
| 2011/0009787 | A1 | 1/2011 | Pallari et al. |
| 2011/0082578 | A1 | 4/2011 | Stanhope et al. |
| 2016/0242947 | A1 | 8/2016 | Zachariasen |
| 2017/0036402 | A1 | 2/2017 | Zachariasen et al. |

OTHER PUBLICATIONS

Berry, E., et al., "Preliminary experience with medical applications of rapid prototyping by selective laser sintering," Med. Eng. Phys, 19(1): 90-96 (1997).

Darling, A.L., et al., "Orthotic design through 3D reconstruction: a passive-assistance ankle-foot orthotic," App. Bion. & Biomech. 3(2): 93-99 (2006).

Dean, D., et al., "Computer Aided Design of Large-Format Prefabricated Cranial Plates," J. Craniofacial Surg. 14(6): 819-32 (Nov. 6, 2003).

Faustini, M.C, et al., "Manufacture of Passive Dynamic Ankle-Foot Orthoses Using Selective Laser Sintering," IEEE Trans Biomed. Eng., 55(2 Pt. 1): 784-90 (Feb. 2, 2008).

* cited by examiner

USE OF ADDITIVE MANUFACTURING PROCESSES IN THE MANUFACTURE OF CUSTOM ORTHOSES

CROSS-REFERENCE TO RELATED APPLICATIONS

This application is a continuation of U.S. patent application Ser. No. 15/479,107 titled USE OF ADDITIVE MANUFACTURING PROCESSES IN THE MANUFACTURE OF CUSTOM ORTHOSES, which was filed on Apr. 4, 2017 ("the '107 application"), which issued as U.S. Pat. No. 10,470,912, on Nov. 12, 2019, which is a continuation of U.S. patent application Ser. No. 14/139,489, titled USE OF ADDITIVE MANUFACTURING PROCESSES IN THE MANUFACTURE OF CUSTOM ORTHOSES, which was filed on Dec. 23, 2013 and issued as U.S. Pat. No. 9,610,731 on Apr. 4, 2017 ("the '489 application"). Claims for priority pursuant to 35 U.S.C. § 119(e) were made in the '489 application to the Dec. 22, 2012 filing date of U.S. Provisional Patent Application No. 61/745,557, titled USE OF ADDITIVE MANUFACTURING PROCESSES IN THE MANUFACTURE OF CUSTOM ORTHOSES ("the '557 Provisional application"), and to the Mar. 15, 2013 filing date of U.S. Provisional Patent Application No. 61/800,582, also titled USE OF ADDITIVE MANUFACTURING PROCESSES IN THE MANUFACTURE OF CUSTOM ORTHOSES ("the '582 Provisional application"). The entire disclosures of the '107 Application, the '489 Application, the '557 Provisional Application, and the '582 Provisional application are hereby incorporated herein.

TECHNICAL FIELD

This disclosure relates generally to methods for manufacturing custom orthoses, such as ankle braces and, more specifically, to use of additive manufacturing processes to manufacture custom orthoses. In addition, this disclosure relates to systems that employ scanning or digitizing equipment and additive manufacturing equipment in the manufacture of custom orthoses, and to custom orthoses that include one or more components that have been fabricated by additive manufacturing processes.

RELATED ART

Custom orthoses, such as braces (e.g., knee braces, ankle braces, etc.), are typically designed to specifically fit the individual for whom they are customized. Customization of an orthosis may optimize the support that the orthosis provides to a body part, such as a joint, to which the orthosis has been fitted. In addition, custom orthoses are typically more comfortable than standard versions of the same types of orthoses, including sized orthoses.

Conventionally, custom orthoses have been made by casting a negative mold of the part of an individual's body that an orthosis is supposed to support. The negative mold is then sent to the orthosis manufacturer, who uses the negative mold to make a positive mold, which generally serves as an accurate replica of the individual's body part. Depending at least partially upon the type of orthosis being made, material may be added to or removed from the positive mold. One or more customized features of the orthosis may then be made on the positive mold, often by hand. From the forgoing, it should be apparent that conventional processes for making custom orthoses are labor intensive and time consuming.

U.S. Pat. No. 6,155,997 to Castro (hereinafter "Castro") discloses an improvement upon the conventional process for making custom orthoses. Specifically, Castro discloses processes for making custom ankle braces. According to Castro, one enhancement to the conventional process for making custom orthoses includes the application of instructions, in the form of readily recognizable symbols, to an inner surface of a negative mold. The instructions may be placed on the inner surface of the negative mold by a person, such as a health care professional, who is prescribing the custom ankle brace. When the brace maker receives the negative mold and uses it to create a positive mold, the instructive symbols that were placed on the inner surface of the negative mold are transferred to corresponding locations on an outer surface of the positive mold. The brace maker may then follow the instructions conveyed by the symbols to define features (e.g., build them up on, remove material from, etc.) the positive mold. Once the brace maker has modified the positive mold in accordance with the instructions conveyed by the symbols, he or she may use the positive mold to make a custom ankle brace. Like other parts of the process, custom ankle braces are also usually made by hand.

Because conventional processes for making custom orthoses (e.g., custom ankle braces, customized portions of knee braces, etc.) may be very labor-intensive, such processes, from casting of a negative mold to completion of the custom orthosis, typically take several weeks (e.g., a month, etc.) to complete. Thus, an individual for whom the orthosis is being made, and who may rely on that orthosis, may have to live without the orthosis for the same amount of time.

SUMMARY

A process for making a custom orthosis according to this disclosure includes the generation of a three-dimensional digital model (e.g., a computer-aided design (CAD) file, etc.) that represents a negative (e.g., a casting, etc.) of a body part for which the orthosis is being made. For the sake of simplicity, the three-dimensional digital model may also be referred to herein as a "digital negative model" or, even more simply, as a "negative model." The negative model may serve as the basis for a customized digital orthosis model, or a custom digital orthosis model, which may be used in conjunction with an additive manufacturing process to make the custom orthosis, or at least a customized portion of the orthosis.

As used hereinafter, "custom orthosis" may refer to an orthosis that has been customized for use with a body part of a particular individual, to a customized portion of an orthosis, or to an orthosis that includes a customized feature. Similarly, the term "orthosis" may be used in reference to an entire orthosis, a part of an orthosis that is to be customized, or to an orthosis and any part thereof that may be customized.

The negative model may be generated by digitizing or scanning (e.g., a three-dimensional scan; a three-dimensional, multi-point analysis from which a three-dimensional model may be extrapolated; a two-dimensional scan that can be used to generate a three-dimensional model; etc.) of the body part for which the orthosis is being made. As used herein, the terms "scan," "scanning" and "scanner" and similar terms relate to techniques for obtaining three or more data points from which a three-dimensional model may be generated, including scanning techniques and digitizing techniques. Thus, the results of scanning a body part may be used to generate a three-dimensional digital model of the body part, which is also referred to herein as a "body part digital model" or as a "body part model." The body part model may then provide a basis for generation of a negative model, which comprises a digital negative model of the body part, which serves as the basis for the contour of one or more surfaces of an orthosis or another medical device.

In some embodiments where digitization or scanning is used to generate a negative model, a body part may be scanned while it is in two or more positions. Such scanning, which is also referred to herein as "dynamic scanning," may be accomplished by incrementally positioning the body part in the two or more positions. As an example, a foot, ankle and/or knee may be scanned while the body part is placed in two or more positions that typically occur as a subject walks (e.g., heel strike, mid-gait, toe-off, etc.). A scan may then be obtained with the body part in each of the incremental positions. Alternatively, the body part may be scanned and two or more images obtained during movement of the body part; for example, while the subject walks (e.g., through at least one cycle of heel strike, mid-gait and toe-off, etc.). A dynamic scan may provide information about how motion of an impaired (e.g., injured, defective, etc.) body part (i.e., unnatural motion) varies from natural motion for that body part. That information may be used to generate a model for a custom orthosis that prevents, or blocks out, unnatural motion while allowing or, or even enabling, natural motion, which facilitates correction of the impairment to the body part.

Alternatively, a negative model may be generated from a negative mold of the body part (e.g., by scanning the negative mold, etc.). In embodiments where a negative mold serves as the basis for the three-dimensional digital model, the negative mold may be made by, or at least ordered by, a health care professional. One or more readily recognizable, optionally standardized symbols or other indicia may be placed at locations where the orthosis is to be modified (e.g., built up, etc.) in a manner prescribed by the health care professional ordering the orthosis or other medical device. Those indicia may convey information for subsequent use by an individual (manual) or computer (automated) while generating a digital orthosis model from data obtained from the negative mold. Negative molds are particularly useful in situations in which a scanner is not readily available to the health care professional. In those situations, and under other circumstances, the negative mold may be sent to a facility, such as a custom orthosis manufacturer, where the negative mold can be scanned to generate the negative model.

As another alternative, a positive physical model of a body part may be used as the basis for the negative model. The positive physical model may be made by any suitable technique. As an example, a negative mold of the body part may be made. The negative mold may then be used to form the positive physical model. One or more readily recognizable, optionally standardized symbols or other indicia may be placed at locations on the positive physical model where an orthosis made using the positive physical model is to be modified (e.g., built up, etc.) in a manner prescribed by the health care professional ordering the orthosis or other medical device. Once the positive physical model has been made, it may be scanned. Data obtained from scanning the positive physical model may then serve as a basis for the negative model. Any indicia on the positive physical model may be transferred to the negative model (e.g., for direction on subsequent modification to be made to a digital orthosis model, etc.) or result in modification of the negative model.

Regardless of how the negative model is obtained or generated, it may be digitally applied to a digital orthosis model, which may define various features of the custom orthosis that will be made based on the negative model. Non-limiting examples of such features of the digital orthosis model include, but are not limited to, the outer periphery of the orthosis, the general shape and/or contour of the orthosis, uncustomized features of the orthosis (e.g., outer surfaces that do not engage or contact the body part, etc.) and connectors for coupling the orthosis or orthosis part to other elements, among other features. When features, such as surface contours, dimensional positioning of two or more features of the body part with which the orthosis will be used and the like, from the negative mold are applied to the digital orthosis model, a customized digital orthosis model, or a custom digital orthosis model, is created.

A negative model and/or a customized digital orthosis model may be modified to accommodate one or more features of a custom orthosis that will be made on the basis of the orthosis model. As an example, one or more portions of a surface of the negative model or customized digital orthosis model may be recessed so that an orthosis or portion of an orthosis manufactured from the customized digital orthosis model can accommodate one or more corresponding features (e.g., reinforcement elements, cushions or pads, etc.). As another example, one or more portions of the surface of the negative model or the customized digital orthosis model may be recessed to accommodate features of the body part, such as bony prominences, bony protrusions or the like. In yet another example, one or more portions of the negative model or the customized digital orthosis model may be built up. By digitally building up one or more portions of the negative model or the customized digital orthosis model, the model may be modified to include one or more corresponding protruding features of a custom orthosis. Such features may perform a variety of functions, including without limitation, supporting a corresponding portion of the body part, applying a desired amount of pressure to a corresponding portion of the body part and/or facilitating proper alignment of a custom orthosis with the body part, to identify only a few.

A surface of the negative model/customized digital orthosis model may be modified to impart different regions of the surface and, optionally, different regions of a custom orthosis that is to be fabricated on the basis of the negative model/customized digital orthosis model, with different rigidities and/or flexibilities. Differences in the rigidities and/or flexibilities of different regions of a custom orthosis may be achieved by using materials of different hardnesses in different regions of the custom orthosis (e.g., softer materials in more flexible regions, harder materials in more rigid regions, etc.).

Once the customized digital orthosis model has been generated and, if desired, modified, it may serve as the basis, or as a three-dimensional blueprint, upon which additive manufacturing equipment relies to define a custom orthosis, or at least a customized portion of an orthosis. Generally, when operating under control of programming based on the customized digital orthosis model, the additive manufacturing equipment may manufacture the custom orthosis as a plurality of adjacent, adhered elements, or sections. The adjacent, adhered elements may be defined and associated with one another in a manner that physically represents the customized digital orthosis model. More specifically, the different elements of a custom orthosis that is made by an additive manufacturing process may comprise layers that are at least partially superimposed with respect to one another.

A customized, form-fitting surface of a custom orthosis may have a contour that is defined by a plurality of adjacent, mutually adhered elements. In various embodiments, the adhered elements have dimensions that impart the finished product with a high degree of definition, including smooth surface contours. Adjacent adhered elements are also permitted to integrate with one another, which eliminates weak points in the finished structure (e.g., discrete boundaries between adjacent elements, etc.) and strengthens it.

Further customization may be achieved when additive manufacturing processes are used that provide for the use of two or more materials (e.g., different materials; materials with different properties, such as hardness; etc.) to define different regions of each element (e.g., layer, etc.). When such a process is used, one or more layers of a custom orthosis may include one or more rigid regions and one or more flexible regions, thus imparting the custom orthosis with a tailored pattern of rigid and flexible features. Without limiting the scope of this disclosure, rigid features may prevent unnatural motion (e.g., excessive movement beyond a normal range of motion, etc.) while enabling a normal range of motion. More flexible features may provide for greater freedom of movement (e.g., for uninjured anatomical structures, for injured anatomical structures of the body part that are experiencing limited range of motion, etc.).

The custom orthosis resulting from an additive manufacturing process may then be assembled with other components of the orthosis, if necessary, and used by the individual for whom it was made. The resulting custom orthosis may have substantially the same properties as, or even improved properties over, a hand-made custom orthosis.

In addition to being useful for manufacturing customized portions of orthoses, techniques that incorporate teachings of this disclosure may be applied to the fabricating of other types of medical devices. By way of non-limiting example, the disclosed processes may be used to fabricate casts, including casts that enable use of a stabilized body part in water and, thus, from which water may be readily removed (i.e., the stabilized body part may be readily dried).

A system that incorporates teachings of this disclosure may include a physical model generation component and a custom orthosis manufacturing component. The physical model generation component may be the office of a health care provider who is prescribing and/or ordering a custom orthosis for one of its patients. The physical model generation component may ship the physical model to a remote custom orthosis manufacturing component. Once the remote custom orthosis manufacturing component receives the physical model, it may manufacture the custom orthosis in accordance with this disclosure within a day or two. In total, this type of system may enable the manufacture of custom orthoses within three days to five days.

Other aspects, as well as features and advantages of various aspects of the disclosed subject matter, will become apparent to those of ordinary skill in the art through consideration of the ensuing description, the accompanying drawings and the appended claims.

DETAILED DESCRIPTION

In various embodiments, processes for making custom orthoses are disclosed and depicted. Although the disclosed embodiments relate to the manufacture of a custom foot bed for an ankle brace, processes that incorporate teachings of this disclosure may also be used to fabricate features of other types of orthoses that are custom-made for use with a body part of a particular individual, and in processes for making entire orthoses.

Figure 1:
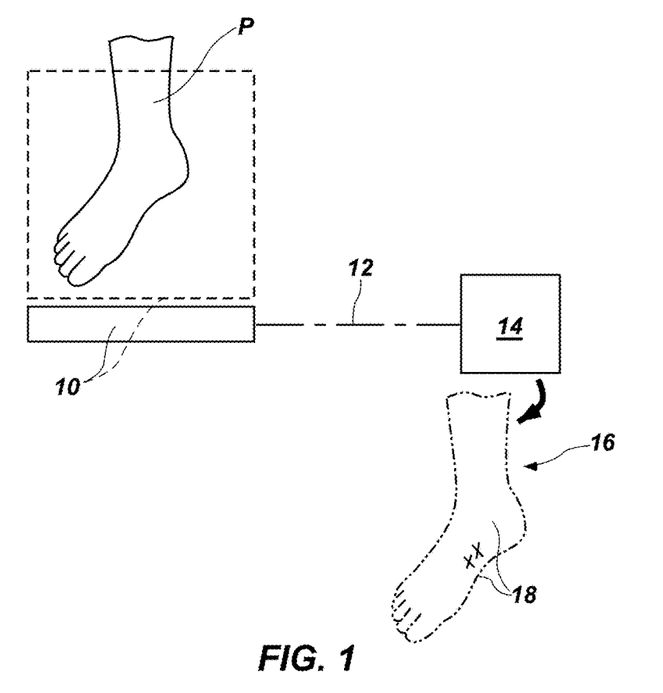
FIG. 1 is a schematic representation of an embodiment of a method for generating a digital negative model of a body part, which includes scanning the body part.

With reference to FIG. 1, an embodiment of a method for obtaining a negative model of a body part P—depicted as the sole of an individual's foot—is illustrated. In such a method, a scanner 10 that has been configured to generate a three-dimensional digital representation of a scanned object may be used to generate a three-dimensional digital representation of the body part P. In some embodiments, the scanner 10 may comprise a digitizer that operates based on a so-called "last," or basic, representation (e.g., based on common dimensions for a particular demographic, etc.) of the body part P being digitized. A digitizer may include a probe, such as a faro arm, that obtains an outline of the body part P at intermittent locations along the body part (e.g., every centimeter, every inch, etc.). These outlines, which provide cross-sections of the body part P, may then be assembled, and data interpolated therebetween to provide a three-dimensional model of the body part P. In other embodiments, the scanner 10 may comprise a three-dimensional scanner of a known type.

The scanner 10 may be configured to obtain a single image of the body part P, or it may be configured to obtain two or more images of the body part P in a corresponding number of positions. A scanner 10 that obtains data while a body part P remains stationary may be used for this purpose by positioning the body part P in a plurality of different, substantially stationary positions while the scanner 10 operates. Alternatively, the scanner 10 may be configured to obtain data on a body part P as the body part P is in motion (e.g., a foot, ankle and/or knee as a subject walks or runs on a treadmill, etc.). Some specific, but non-limiting embodiments of such a scanner include one or more fluoroscopes or similar devices that obtain multiple images during movement, motion capture equipment and the like. Of course, other apparatuses that provide data that may be used to generate a three-dimensional model may also be employed as the scanner 10.

The scanner 10 may transmit data 12 obtained from scanning the body part P to a processing element 14, such as a computer processor. The processing element 14, under control of one or more programs, may generate a digital, three-dimensional, negative model of the body part P, or "digital negative model" 16 or "negative model." The digital negative model 16 may include data that represents one or more surfaces 18 that are contoured and arranged complementarily to, or as negatives of, one or more corresponding surfaces of the body part P. The one or more surfaces 18 of the digital negative model 16 may represent surface contours that will ultimately be included in a custom orthosis.

Figure 2:
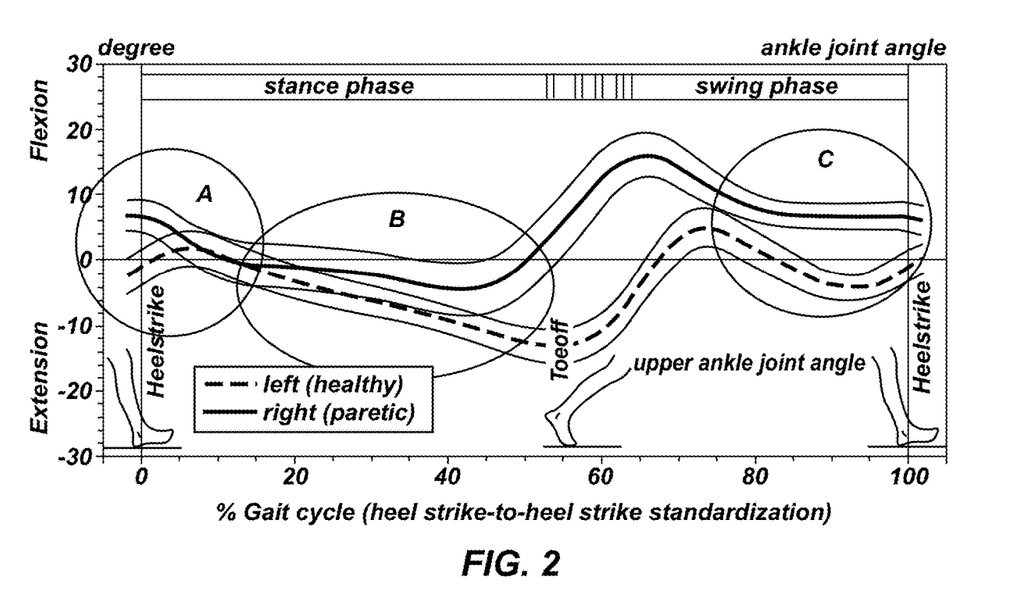
FIG. 2 is an impact curve obtained as a subject with an impaired foot walked on a treadmill.
Figure 3:
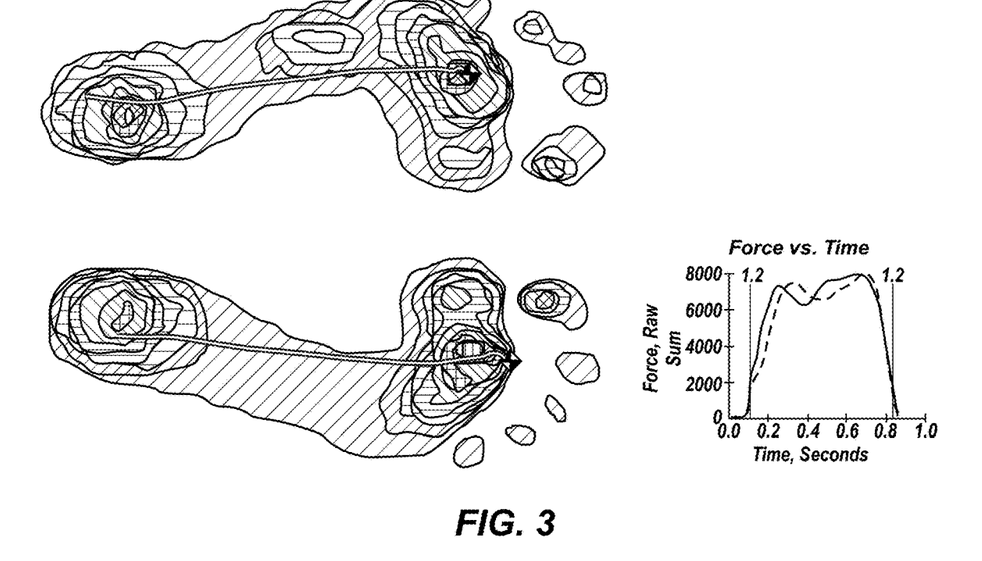
FIG. 3 is an impact force diagram of the forces experienced by the impaired foot as the subject walked on the treadmill.

In embodiments where the data 12 obtained by the scanner 10 corresponds to two or more chronological positions of the body part P, the data 12 may provide additional insight as to the specific anatomical cause or causes of any impairment of the body part P. Such data 12 may be compared with other data on the body part P. As a non-limiting example, data 12 obtained during a plurality of scans of a foot in motion throughout gait, which data 12 corresponds to the anatomy of the foot throughout gait, may be compared with other data (e.g., an impact curve (see FIG. 2), an impact force diagram (see FIG. 3), etc.) obtained as the subject walks or runs. Abnormalities in such other data may be useful in identifying a specific anatomical cause or causes of each abnormality. Each anatomical cause may then be addressed while generating the digital negative model 16. Accordingly, the digital negative model 16 may account for the dynamic range of the body part P.

Figure 4:
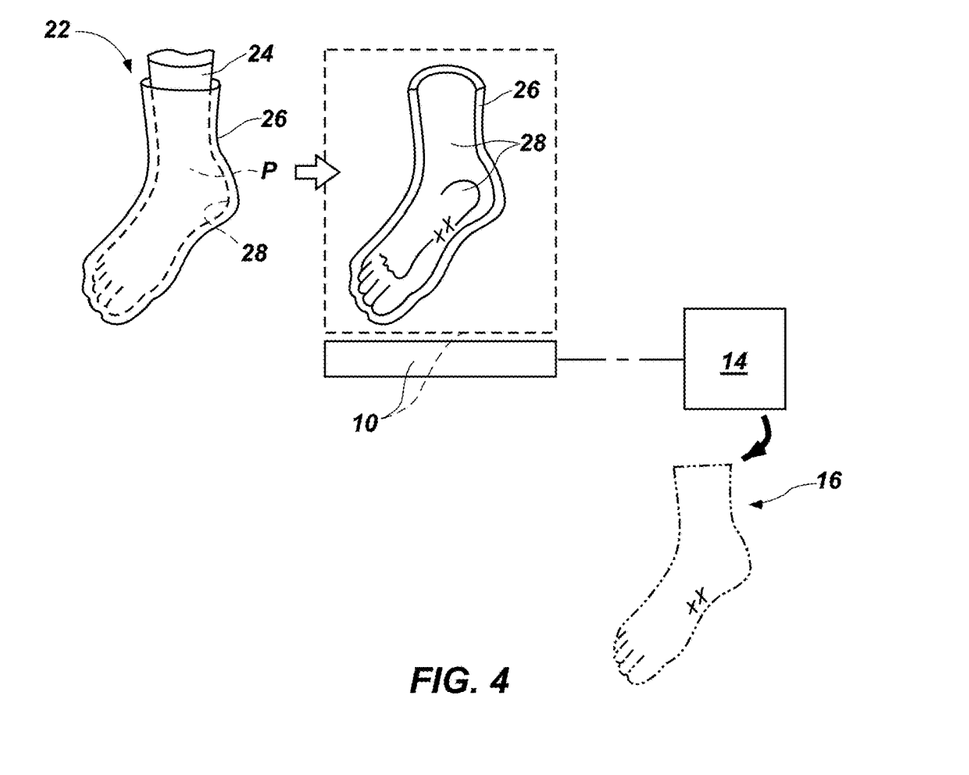
FIG. 4 is a schematic representation of another embodiment of a method for generating a digital negative model of a body part, in which a physical negative mold, or cast, is formed, then scanned.

As an alternative to directly scanning a body part P to generate a digital negative model 16, a digital negative model 16 may be obtained from a physical negative model, or cast 26, of the body part P, as illustrated by FIG. 4. A variety of processes may be used to make one or more physical negative models 22 of the body part P. Without limitation, such a method may include positioning a thin, form-fitting element 24 over the body part P. A cast 26 (e.g., a plaster cast, a fiberglass cast, etc.) may then be built up on the form-fitting element 24 and around the body part P in a manner that causes an inner surface 28 of the cast 26 to substantially assume the shape of the body part P. In some embodiments, the cast 26 may be built up without deforming the shape of the body part P or any of its surfaces. Once the cast 26 has hardened, it may be removed (e.g., from the body part P, etc.).

Once the cast 26 has been removed from a body part P for which an orthosis, such as an ankle brace, is being customized, the cast 26 may function as a physical negative model 22 of the body part P. More specifically, the cast 26, as a physical negative model 22, in one or more sections, may be scanned by a scanner 10 to obtain digital data 12 representative of the cast 26, and that data 12 may be processed by a processing element 14, which may then generate a digital, three-dimensional negative model or "digital negative model" 16 or "negative model," of the body part P or portion thereof.

Figure 5:
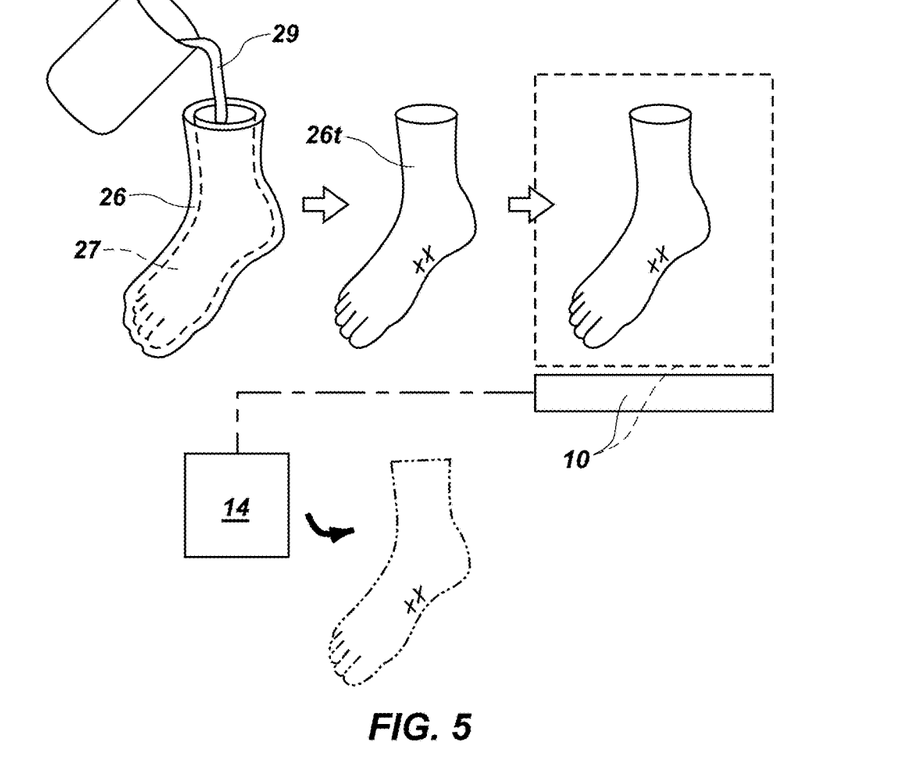
FIG. 5 is a schematic representation of yet another embodiment of a method for generating a digital negative model of a body part, in which a mold, or cast, is formed, then used to form a positive physical model, which is then scanned.

FIG. 5 is a schematic representation of a process in which a cast 26 of a body part P is formed, as described in reference to FIG. 4, and then the cast 26 used to form a positive physical model 26+ of the body part P. The positive physical model 26+ may be formed by any suitable manner known in the art. Without limitation, a flowable, hardenable material 29 (e.g., a liquid resin, plaster, etc.) may be introduced into a cavity 27 of the cast 26. As the flowable, hardenable material 29 solidifies, it forms the positive physical model 26+, and the cast 26 may be removed from the positive physical model 26+. The positive physical model 26+ may then be scanned, and the data 12 obtained from scanning may be used to generate a digital negative model 16 of the body part P or a portion thereof.

In various embodiments, one or more symbols X may be used on a cast 26, a positive physical model 26+ and/or a digital negative model 16 to identify regions of an orthosis that are to be modified in a manner that differs from the contour of a portion of a body part P with which the orthosis is to be used. A symbol X may comprise a readily recognizable, even standardized, indicia that enables an individual (manually) or a computer (automatically) to identify the manner (e.g., location(s), extent(s), etc.) in which an orthosis is to be modified (e.g., areas that are to be built up, areas that are to be formed from a material with a hardness that differs from a hardness of a remainder of the orthosis, recessed areas, etc.). The modification that corresponds to a particular symbol X may be transferred to the digital negative model 16 for subsequent use, or the modification that corresponds to that symbol X may be incorporated into the digital negative model 16 (i.e., the digital negative model 16 may be modified). The symbol X may signal to an individual that certain modifications are to be made to the digital negative model 16 or a customized digital orthosis model 40 (see FIG. 6), and the individual may manually make a modification that corresponds to each symbol X. Alternatively, each symbol X may be configured to be recognized by a processing element that generates the digital negative model 16 or applies the digital negative model 16 to a digital orthosis model 30 (see FIG. 6), and the processing element may incorporate the appropriate modification into the digital negative model 16 or the customized digital orthosis model 40.

Figure 6:
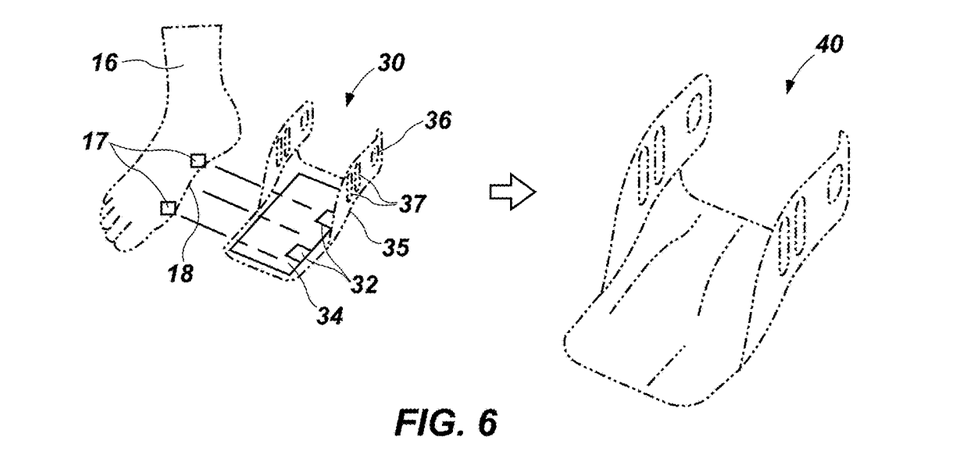
FIG. 6 provides a representation of application of a digital negative model to an orthosis model to generate a customized digital orthosis model.

Turning now to FIG. 6, once a digital negative model 16 of an individual's body part P has been generated (and regardless of the manner in which digital negative model 16 was generated), the digital negative model 16 may be applied to (e.g., overlaid with, etc.) a digital orthosis model 30 (e.g., by processing element 14, another processing element, etc.). The digital orthosis model 30 may include a customizable portion 34, as well as standard features, such as an outer periphery 35, one or more coupling elements 36 (e.g., hinge elements, etc.), one or more stiffening features 37 (e.g., the illustrated gussets, etc.), among other standard features.

In a specific embodiment, the digital negative model 16 may be applied to the digital orthosis model 30 by identifying two or more features 17 on the digital negative model 16 that correspond to predetermined reference features 32 on a digital orthosis model 30. The corresponding features 17 and 32 may then be aligned with one another, effectively superimposing the digital negative model 16 over at least a customizable portion 34 of the digital orthosis model 30. Any data from the digital negative model 16 located outside the customizable portion 34 of the digital orthosis model 30 may be discarded. The remaining data from the digital negative model 16, including data representative of the one or more surfaces 18 that complement, or are negatives, of surfaces of the body part P for which a custom orthosis is being manufactured, may be applied to the customizable portion 34 of the digital orthosis model 30 (i.e., it may be incorporated into the digital orthosis model 30 to define a customized digital orthosis model 40.

Figure 7:
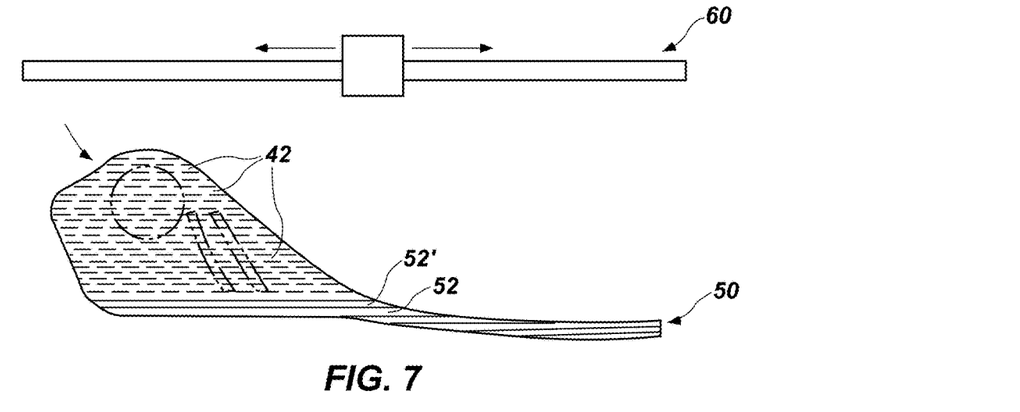
FIG. 7 illustrates an embodiment of a process in which a customized digital orthosis model provides a pattern for fabrication of a custom orthosis by way of an additive manufacturing process.

Once a customized digital orthosis model 40 has been generated, it may be processed and used to form a custom orthosis 50 (FIG. 7) or at least a portion of a custom orthosis 50. FIG. 7 schematically illustrates an embodiment of a method for manufacturing, or fabricating, a custom orthosis 50 from a customized digital orthosis model 40. As an example of such a method, an additive manufacturing process, such as that effected by the systems available from Objet Geometries, Ltd., of Rehovot, Israel, may be used fabricate some or all of the custom orthosis 50 as a series of layers. When such a process is used, the customized digital orthosis model 40 may be separated into a plurality of sections 42, such as slices or layers (e.g., the customized digital orthosis model 40 may be converted from a CAD (Computer Aided Design) format to any suitable format, such as an STL (or .stl) (STereoLithography) format, etc.).

Each of the sections 42 of the customized digital orthosis model 40 may be used by an additive manufacturing system 60 to define a corresponding section 52 of a custom orthosis 50. More specifically, the additive manufacturing system 60 may be used to fabricate the custom orthosis 50, as well as any contoured surfaces that are intended to fit to the form, or contour, of a body part P (FIGS. 1 and 4), one section 52 (e.g., layer, etc.) at a time. As each section 52 is formed, the material from which it is formed may cure or otherwise solidify. Once a section 52 has at least partially solidified (e.g., before that section 52 has fully cured, etc.), a subsequent section 52' may be formed adjacent to it (e.g., at least partially superimposed over it, etc.). The subsequent section 52' may be formed before the previously formed, adjacent section 52 has fully cured, enabling at least some integration between the adjacent sections 52 and 52', which may impart a custom orthosis 50 that results from such a process with substantially smooth surfaces, increase the fracture resistance (and, optionally, the flexibility) of the custom orthosis 50, increase the strength of the custom orthosis 50, otherwise improve the custom orthosis 50 or provide any combination of the foregoing. Alternatively, one section 52 may substantially cure or fully cure before the subsequent section 52' is formed, resulting in a structure with a discernable, discrete boundary between the adjacent sections 52 and 52'. In either event, the resulting structure includes a plurality of adjacent, mutually adhered sections 52 (e.g., a plurality of at least partially superimposed, mutually adhered layers, etc.). Such a process may be used to form a customized portion of the custom orthosis 50, an entire part of the custom orthosis 50, or the entire custom orthosis 50.

When the additive manufacturing system 60 includes a so-called "3D printer," such as that manufactured by Objet, and a polypropylene-like material, such as the Durus-White™ material available from Objet, is used to form at least a portion of the custom orthosis, each section 52 (e.g., layer, etc.) may have a thickness of about 0.005 inch to about 0.001 inch or less. The smoothness of the surfaces of the custom orthosis 50 corresponds, at least in part, to the thinness of the sections 52 from which the custom orthosis 50 is formed, with thinner sections 52 forming smoother surfaces.

Figure 8:
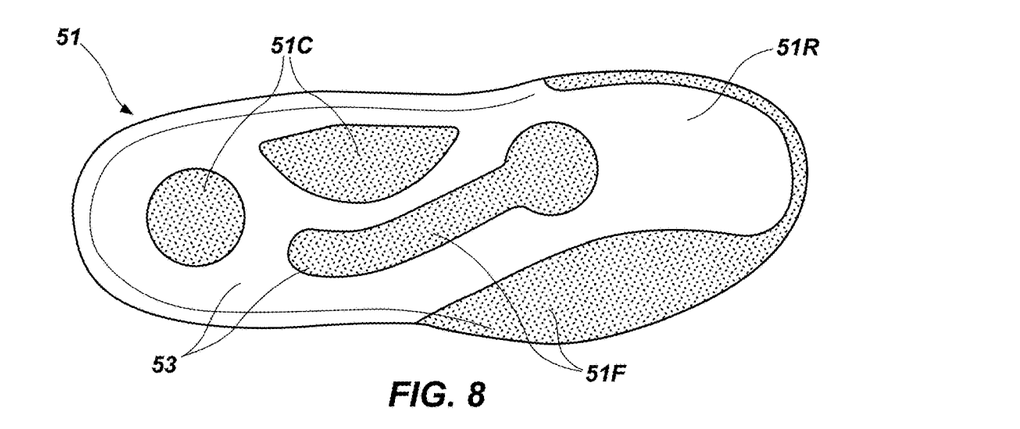
FIG. 8 illustrates an embodiment of a part of a custom orthosis fabricated in accordance with the method depicted by FIG. 7 and including at least one layer with at least one rigid region and at least one flexible region, which define rigid and flexible regions of the part.

In some embodiments, two or more materials may be co-deposited (e.g., as part of the same section 52 (e.g., layer, etc.), as different sections 52 (e.g., layers, etc.), as combinations of the foregoing, etc.) to form at least part of a custom orthosis 50. As an example, a majority of the custom orthosis 50 may be fabricated from a material that imparts the custom orthosis 50 with one or more desired characteristics (e.g., rigidity, durability, etc.), while another material may form a coating on at least part of the custom orthosis 50 to provide it with added characteristics (e.g., flexibility, cushioning, etc.). FIG. 8 shows a specific embodiment of part of a custom orthosis 50 (FIG. 7) in which each of one or more sections 52 (FIG. 7) (e.g., a layer that forms a surface of the part, a plurality of layers adjacent to a surface of the part, etc.) is defined from two or more materials with different characteristics. More specifically, FIG. 8 illustrates an embodiment of a foot bed 51 of a custom orthosis 50, with a rigid region 51R and a plurality of flexible regions 51F. More specifically, the rigid region 51R may be defined by a material having a hardness of about 90 Shore A or greater durometer, while each flexible region 51F may have a hardness of about 30 Shore A to about 40 Shore A. In addition, the foot bed 51 includes cushions 51C, which may comprise an integral part of one or more sections 52 (e.g., layers, etc.) of the foot bed 51, or which may be applied to a surface 53 of the foot bed 51. The embodiment of foot bed 51 illustrated by FIG. 8 includes an elongated, curved flexible region 51F that generally follows the path of the fundamental longitudinal arch of the foot, and a lateral flexible region 51F located beneath the fifth metatarsal (i.e., the small toe, or "pinkie toe"). The curved flexible region 51F may allow the foot to flex where it naturally wants to flex. The lateral flexible region 51F may provide for flexibility in the mid-stance and toe-off phases of a subject's gait. A portion of the rigid region 51R adjacent to the curved flexible region 51F may define an arch support that prevents the arch of the foot from collapsing. Cushions 51C may be provided on the arch support and beneath the heel for comfort.

As another example, a first material may be used to form sections 52 (e.g., layers or other adhered elements) of a majority of the custom orthosis 50, while a second material (e.g., a softer material, etc.) may be used to form a plurality of adjacent, mutually adhered sections 52 (e.g., layers or other adhered elements) that define features (e.g., cushioned areas, etc.) of the custom orthosis 50.

In embodiments wherein the custom orthosis 50 comprises only part of an orthosis, the custom orthosis may be assembled with one or more standard elements of the orthosis.

A system according to this disclosure may include a three-dimensional scanner 10, at least one processing element 14 and an additive manufacturing system 60, which may perform the above-disclosed functions. Additionally, such a system may include a component in which a cast 26, or negative model, of a body part is obtained, as well as an assembly component, in which a custom orthosis 50 may be assembled with one or more standard orthosis elements to define a complete orthosis.

When additive manufacturing processes are used to fabricate a custom orthosis 50, the labor-intensive processes of hand-forming a positive model and making an orthosis may from such a physical model be eliminated. Thus, the amount of time it takes to make a custom orthosis 5 may be significantly reduced. In some embodiments, it may be possible to reduce the time it takes to make a custom orthosis from two weeks or more to as little as three to five days.

Figure 9:
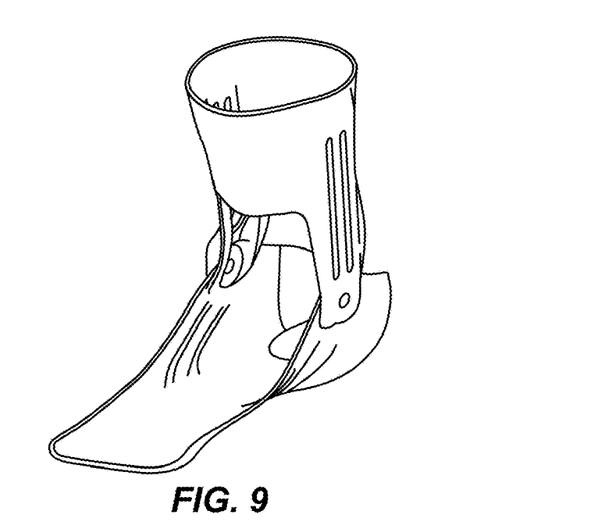
FIG. 9 shows an embodiment of a custom orthosis.

In a specific embodiment, the foregoing processes may be used to form one or more surfaces of an ankle brace, such as that depicted by FIG. 9. The embodiment of ankle brace depicted by FIG. 9 includes an upper element, which is configured to be positioned around an ankle and to hold the ankle brace in place, and a bottom element that comprises the embodiment of custom orthosis 50 shown in FIGS. 6 and 7. In some embodiments, the upper element may comprise an off-the-shelf component that may have a standard shape and one of a limited number (e.g., one, three, five, etc.) of standard sizes. The use of one or more standard components in the manufacture of a custom (or at least partially custom) orthosis may decrease the amount of time required to make the orthosis and minimize the cost of a custom orthosis. In other embodiments, however, the disclosed processes may be used to fabricate two or more components of an orthosis, such as both the upper element and the lower element of the depicted ankle brace.

Custom orthotic components may be desirable in a variety of situations, including those where a standard component will not fit a particular body part (e.g., the contour on the bottom of a foot, etc.) in a desired manner, and the standard component cannot be adjusted in a manner that will provide the desired fit.

Although the foregoing description contains many specifics, these should not be construed as limiting the scopes of the inventions recited by any of the appended claims, but merely as providing information pertinent to some specific embodiments that may fall within the scopes of the appended claims. Features from different embodiments may be employed in combination. In addition, other embodiments may also lie within the scopes of the appended claims. All additions to, deletions from and modifications of the disclosed subject matter that fall within the scopes of the claims are to be embraced by the claims.

What is claimed:

1. A method for fabricating a custom orthosis, comprising:
generating, from data obtained from a body part, a digital model corresponding to a surface of the body part;
applying a negative of the digital model to a digital orthosis model to incorporate a custom surface data into a customizable area of the digital orthosis model to create a custom digital orthosis model; and
using the custom digital orthosis model to directly fabricate the custom orthosis for use with the body part.

2. The method of claim 1, further comprising:
scanning the body part for which the custom orthosis is to be made to provide the data for generating the digital model.

3. The method of claim 2, wherein scanning the body part comprises obtaining a plurality of scans of the body part.

4. The method of claim 1, further comprising:
incorporating a modification to be made to the custom orthosis into at least one of the data obtained from the body part, the digital model of the body part, and the negative of the digital model.

5. The method of claim 1, wherein applying the negative of the digital model to the digital orthosis model comprises applying the negative to the digital orthosis model including at least one standard feature.

6. The method of claim 1, wherein using the custom digital orthosis model comprises separating the custom digital orthosis model into a plurality of sections.

7. The method of claim 6, wherein using the custom digital orthosis model to fabricate the custom orthosis comprises sequentially defining a plurality of adjacent sections of the custom orthosis, at least one section being formed adjacent to and adhered to a previously formed section of the custom orthosis.

8. The method of claim 6, wherein using the custom digital orthosis model to fabricate the custom orthosis comprises:
fabricating a section of the custom orthosis; and
fabricating a subsequent section in contact with a previously formed section.

9. The method of claim 1, wherein using the custom digital orthosis model to directly fabricate the custom orthosis comprises fabricating the custom orthosis from a plurality of different materials.

10. The method of claim 9, wherein fabricating the custom orthosis from the plurality of different materials comprises co-depositing the plurality of different materials.

11. The method of claim 10, wherein co-depositing the plurality of different materials comprises co-depositing the plurality of different materials as part of a same section of the custom orthosis.

12. The method of claim 10, wherein co-depositing the plurality of different materials comprises depositing each material of the plurality of different materials to define a corresponding section of the custom orthosis.

13. A custom orthosis, comprising:
a plurality of adjacent, mutually adhered sections, at least one section of the plurality of adjacent, mutually adhered sections defining a custom surface shaped complementarily to an individual's body part with which the custom orthosis is to be used.

14. The custom orthosis of claim 13, wherein the custom surface is defined by at least a portion of at least one section of the plurality of adjacent, mutually adhered sections and by at least a portion of another, adjacent section of the plurality of adjacent, mutually adhered sections.

15. The custom orthosis of claim 13, wherein the custom surface is a substantially smooth surface.

16. The custom orthosis of claim 13, wherein the custom surface contains at least one modification that deviates from a shape of a surface of the individual's body part that corresponds to the custom surface.

17. The custom orthosis of claim 16, wherein the at least one standard feature is defined by at least some of the plurality of adjacent, mutually adhered sections.

18. The custom orthosis of claim 17, wherein the adjacent regions of different hardnesses are defined in a same section of the plurality of adjacent, mutually adhered sections.

19. The custom orthosis of claim 13, further comprising:
at least one standard feature.

20. The custom orthosis of claim 13, comprising adjacent regions of different hardnesses adjacent to one another.

* * * * *